United States Patent
Sianawati

(10) Patent No.: US 10,212,946 B2
(45) Date of Patent: Feb. 26, 2019

(54) MICROBICIDAL COMPOSITION

(71) Applicant: Dow Global Technologies LLC, Midland, MI (US)

(72) Inventor: Emerentiana Sianawati, Collegeville, PA (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 82 days.

(21) Appl. No.: 15/108,478

(22) PCT Filed: Dec. 10, 2014

(86) PCT No.: PCT/US2014/069512
§ 371 (c)(1),
(2) Date: Jun. 27, 2016

(87) PCT Pub. No.: WO2015/102832
PCT Pub. Date: Jul. 9, 2015

(65) Prior Publication Data
US 2016/0324164 A1 Nov. 10, 2016

Related U.S. Application Data

(60) Provisional application No. 61/921,618, filed on Dec. 30, 2013.

(51) Int. Cl.
| | |
|---|---|
| A61K 36/00 | (2006.01) |
| A01N 65/22 | (2009.01) |
| A23L 3/3544 | (2006.01) |
| A01N 43/80 | (2006.01) |
| A61K 8/49 | (2006.01) |
| A61L 2/16 | (2006.01) |
| A61L 2/18 | (2006.01) |
| A61L 9/013 | (2006.01) |
| C02F 1/50 | (2006.01) |
| C09D 5/14 | (2006.01) |
| A61Q 19/00 | (2006.01) |
| A61K 8/92 | (2006.01) |
| C11D 7/32 | (2006.01) |
| C11D 3/48 | (2006.01) |
| A61K 36/53 | (2006.01) |
| A01N 25/34 | (2006.01) |
| C09D 7/63 | (2018.01) |
| C02F 103/00 | (2006.01) |
| C02F 103/02 | (2006.01) |
| C02F 103/42 | (2006.01) |
| C08K 5/00 | (2006.01) |

(52) U.S. Cl.
CPC .............. *A01N 65/22* (2013.01); *A01N 25/34* (2013.01); *A01N 43/80* (2013.01); *A23L 3/3544* (2013.01); *A61K 8/49* (2013.01); *A61K 8/922* (2013.01); *A61K 36/53* (2013.01); *A61L 2/16* (2013.01); *A61L 2/18* (2013.01); *A61L 9/013* (2013.01); *A61Q 19/00* (2013.01); *C02F 1/50* (2013.01); *C09D 5/14* (2013.01); *C09D 7/63* (2018.01); *C11D 3/48* (2013.01); *C11D 7/3281* (2013.01); *A61K 2800/10* (2013.01); *A61K 2800/524* (2013.01); *A61L 2202/24* (2013.01); *C02F 2103/008* (2013.01); *C02F 2103/023* (2013.01); *C02F 2103/42* (2013.01); *C02F 2303/04* (2013.01); *C08K 5/0058* (2013.01)

(58) Field of Classification Search
CPC ...................................................... A61K 36/00
See application file for complete search history.

(56) References Cited

U.S. PATENT DOCUMENTS

| | | |
|---|---|---|
| 3,821,389 A | 6/1974 | Grivas |
| 6,548,085 B1 | 4/2003 | Zobitne et al. |
| 2005/0019434 A1 | 1/2005 | Duvert et al. |
| 2007/0078118 A1 | 4/2007 | Levy et al. |
| 2009/0257958 A1 | 10/2009 | Sims |

FOREIGN PATENT DOCUMENTS

| | | | | |
|---|---|---|---|---|
| CN | 102239893 A | * | 11/2011 | |
| EP | 0920860 A2 | | 6/1999 | |
| GB | 861379 A | * | 2/1961 | ........... A61K 31/425 |
| GB | 1531431 A | | 11/1978 | |

* cited by examiner

Primary Examiner — Qiuwen Mi
(74) Attorney, Agent, or Firm — Tifani M. Edwards

(57) ABSTRACT

Synergistic microbicidal compositions containing N-methyl-1,2-benzisothiazolin-3-one and essential oils.

2 Claims, No Drawings

MICROBICIDAL COMPOSITION

This invention relates to a synergistic combination of a selected microbicides having greater activity than would be observed for the individual microbicide.

Since early times, essential oils have been used to flavor or enhance fragrances in the perfume, pharmaceutical, cosmetic and food industries, and as healing and therapeutic active ingredients in folk medicine and aromatherapy. Essential oils, which consist of aromatic and volatile liquids extracted from plants, contain chemicals (secondary metabolites) that play a role in plant defense against pests and often possess antimicrobial properties. The antibacterial properties of essential oils and their constituents have been documented extensively. For example, the essential oil of rosemary has shown antimicrobial power and effectiveness in controlling the growth of various gram positive and negative bacteria. The use of thyme oil as a preservative for topically applied cosmetic formulations has also been investigated and proven to be quite effective. As various industries (household products, personal care, and building materials) are moving toward the use of more natural products, the interest in essential oils as natural preservatives has been amplified. However, a significant problem resulting from the use of essential oils as preservatives is that they are most often not potent enough as a single biocide component and are frequently required at very high concentrations for effective preservation. As a result, negative organoleptic effects can be experienced. There is a need for an composition that provides enhanced preservation effectiveness, maximized cost efficacy and minimum organoleptic effects.

Moreover, in some cases individual organic microbicides cannot provide effective control of microorganisms, even at high use concentrations, due to weak activity against certain types of microorganisms, e.g., those resistant to some microbicides, or due to aggressive environmental conditions. Combinations of different microbicides are sometimes used to provide overall control of microorganisms in a particular end use environment. For example, U.S. Pat. App. Pub. No. 2007/0078118 discloses synergistic combinations of N-methyl-1,2-benzisothiazolin-3-one (MBIT) with other biocides. However, there is a need for additional combinations of microbicides having enhanced activity against various strains of microorganisms to provide effective control of the microorganisms. Moreover, there is a need for combinations containing lower levels of individual microbicides for environmental and economic benefit. Currently markets like the home and personal care market are looking for products based upon natural ingredients. While MBIT is an ingredient often used in the home and personal care market it would be advantageous to be able to minimize the amount of MBIT used and combine it with a natural ingredient, while maintaining the same or better effectiveness.

The problem addressed by this invention is to provide such additional combinations of microbicides.

The present invention is directed to a microbicidal composition comprising: (a) N-methyl-1,2-benzisothiazolin-3-one; and (b) at least one essential oil.

The invention is also directed to a method of inhibiting the growth of or controlling the growth of microorganisms comprising the step of adding the microbicidal composition to an industrial process water; ultrafiltration; industrial or consumer adhesives; household products; cosmetics; toiletries; shampoos; soaps; detergents; industrial cleaners; floor polishes; laundry rinse water; medical devices; diagnostic reagent preservation; food, beverage, and industrial process pasteurizers; toilet bowls; recreational water; pools; and spas.

Additionally, according to the present invention there is provided a coating composition comprising: (a) N-methyl-1,2-benzisothiazolin-3-one; and (b) at least one essential oil wherein the weight ratio of N-methyl-1,2-benzisothiazolin-3-one to essential oil is from 1:52 to 1:160,000.

Also, the invention is directed to a product comprising N-methyl-1,2-benzisothiazolin-3-one; and at least one essential oil wherein the weight ratio of N-methyl-1,2-benzisothiazolin-3-one to essential oil is from 1:52 to 1:160,000.

Lastly, the invention is directed to a dry film made by a process comprising applying a layer of the aforementioned coating composition to a substrate and drying the coating composition or allowing the coating composition to dry.

As used herein, the following terms have the designated definitions, unless the context clearly indicates otherwise. "MBIT" is N-methyl-1,2-benzisothiazolin-3-one. The term "essential oil" refers to a hydrophobic liquid containing volatile aroma compounds derived from plants. Examples of essential oil include oil such as mineral oil, wintergreen oil, castor oil, pine oil, almond oil, citronella oil, thyme oil, and rosemary oil. Essential oils of the present invention include thyme oil CAS No. 8007-46-3 and rosemary oil CAS No. 8000-25-7. The term "microbicide" synonymous with "antimicrobial" refers to a compound capable of killing, inhibiting the growth of or controlling the growth of microorganisms at a locus; microbicides include bactericides, fungicides and algaecides.

The term "microorganism" includes, for example, fungi (such as yeast and mold), bacteria and algae, preferably fungi and bacteria The term "locus" refers to an industrial system or product subject to contamination by microorganisms. The following abbreviations are used throughout the specification: ppm=parts per million by weight (weight/weight), mL=milliliter, ATCC=American Type Culture Collection, MBC=minimum biocidal concentration, and MIC=minimum inhibitory concentration. Unless otherwise specified, temperatures are in degrees centigrade (° C.), and references to percentages (%) are by weight. Amounts of organic microbicides are given on an active ingredient basis in ppm (w/w).

The compositions of the present invention unexpectedly have been found to provide enhanced microbicidal efficacy at a combined active ingredient level lower than that of the individual microbicides. Additional microbicides beyond those listed in the claims may be present in the composition.

The antimicrobial composition comprises N-methyl-1,2-benzisothiazolin-3-one and an essential oil.

In some compositions of the present invention, the antimicrobial composition comprises N-methyl-1,2-benzisothiazolin-3-one and thyme oil. Preferably, a weight ratio of N-methyl-1,2-benzisothiazolin-3-one to thyme oil is from 1:52 to 1:160,000.

In some compositions of the present invention, the antimicrobial composition comprises N-methyl-1,2-benzisothiazolin-3-one and rosemary oil. Preferably, a weight ratio of N-methyl-1,2-benzisothiazolin-3-one to rosemary oil is from 1:250 to 1:16,000.

The microbicides in the composition of this invention may be used "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycerin, glycol ethers; such as propylene glycol ether, diethyleneglycol monobutyl ether, dipropymyne glycol methyl ether, ethylene glycol ethylether, ethylene glycol monobutyl ether; alcohols, such as methanol, ethanol, propanol, isopropanol, phenethyl alcohol, phenoxyethanol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; and mixtures thereof. It is preferred that the solvent is selected from water, glycols, glycol ethers, esters and mixtures thereof. Suitable solid carriers include, for example, cyclodextrin, silicas, clay, animal fat, diatomaceous earth, waxes, cellulosic materials, alkali and alkaline earth (e.g., sodium, magnesium, potassium) metal salts (e.g., chloride, nitrate, bromide, sulfate), and charcoal.

When a microbicide component is formulated in a solvent, the formulation may optionally contain surfactants. When such formulations contain surfactants, they are generally in the form of emulsifiable concentrates, emulsions, microemulsive concentrates, or microemulsions. Emulsifiable concentrates form emulsions upon the addition of a sufficient amount of water. Microemulsive concentrates form microemulsions upon the addition of a sufficient amount of water. Such emulsive and microemulsive concentrates are generally well known in the art; it is preferred that such formulations are free of surfactants. U.S. Pat. No. 5,444,078 may be consulted for further general and specific details on the preparation of various microemulsions and microemulsive concentrates.

A microbicide component also can be formulated in the form of a dispersion. The solvent component of the dispersion can be an organic solvent or water, preferably water. Such dispersions can contain adjuvants, for example, co-solvents, chelants or sequestrants, amines, thickeners, antifreeze agents, dispersants, fillers, pigments, surfactants, biodispersants, sulfosuccinates, terpenes, furanones, polycations, stabilizers, scale inhibitors and anti-corrosion additives.

Those skilled in the art will recognize that the microbicide components of the present invention may be added to a locus sequentially, simultaneously, or may be combined before being added to the locus. It is preferred that the first microbicide and the second microbicide component be added to a locus simultaneously or sequentially. When the microbicides are added simultaneously or sequentially, each individual component may contain adjuvants, such as, for example, solvent, thickeners, anti-freeze agents, colorants, sequestrants (such as ethylenediamine-tetraacetic acid, ethylenediaminedisuccinic acid, iminodisuccinic acid and salts thereof), dispersants, surfactants, biodispersants, sulfosuccinates, terpenes, furanones, polycations, stabilizers, scale inhibitors and anti-corrosion additives.

The microbicidal compositions of the present invention can be used by introducing a microbicidally effective amount of the compositions onto, into, or at a locus subject to microbial attack. Suitable loci include, for example: industrial process water; electrocoat deposition systems; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners and sanitary wipes; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, wallboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

Preferably, the microbicidal compositions of the present invention are used to inhibit the growth of microorganisms at a locus selected from one or more of an industrial process water; ultrafiltration; industrial or consumer adhesives; household products; cosmetics; toiletries; shampoos; soaps; detergents; industrial cleaners; floor polishes; laundry rinse water; medical devices; diagnostic reagent preservation; food, beverage, and industrial process pasteurizers; toilet bowls; recreational water; pools; and spas.

The specific amount of the composition of this invention necessary to inhibit or control the growth of microorganisms and higher aquatic life forms in a locus depends upon the particular locus to be protected. Typically, the amount of the composition of the present invention to control the growth of microorganisms in a locus is sufficient if it provides from 0.1 to 1,000 ppm of the isothiazoline ingredient of the composition in the locus. It is preferred that the isothiazolone ingredients of the composition be present in the locus in an amount of at least 0.5 ppm, more preferably at least 4 ppm and most preferably at least 10 ppm. It is preferred that the isothiazolone ingredients of the composition be present in the locus in an amount of no more than 1000 ppm, more preferably no more than 500 ppm, and most preferably no more than 200 ppm.

The microbicidal compositions of the present invention may be included in a coating composition. N-methyl-1,2-benzisothiazolin-3-one and the at least one essential oil may be added to the coating composition separately or as a mixture or any combination thereof. Preferred coating compositions are liquid. Coating compositions may be aqueous or non-aqueous. Aqueous coating compositions generally contain 30% or more water by weight of the mixture, based on the weight of the coating composition.

Among embodiments in which -methyl-1,2-benzisothiazolin-3-one and the at least one essential oil are included in paint or other coating composition, preferred coating compositions are liquid compositions, especially compositions that contain dispersions of polymers in aqueous media.

Coating compositions are designed so that a layer of the coating composition can readily be applied to a substrate and then dried or allowed to dry to form a dry film. Coating compositions contain a binder. Binders contain one or more of the following: one or more polymer, one or more oligomer, and/or one or more monomer. Oligomers and monomers in binders are designed to polymerize and/or crosslink during or after the formation of the dry film. Polymers in a binder may or may not be designed to crosslink during or after the formation of the dry film.

Coating compositions optionally contain one or more pigment. A pigment is a mineral or an organic substance in the form of small solid particles. Pigments provide full or partial opacity to the dry film.

The antimicrobial compound combinations are useful for preservation of the dry film coating resulting after application of paint or other liquid coating composition. Preferably, the antimicrobial composition is an aqueous latex paint comprising one or more of the antimicrobial compound combinations disclosed herein, or the dry film coating resulting from application of the paint to a surface. An aqueous latex paint is an aqueous liquid coating composition in which the binder is a polymer in the form of a latex (i.e., in the form of polymer particles dispersed throughout the water). More preferred are aqueous latex paints in which the binder contains one or more acrylic polymer.

The present invention also encompasses a method for preventing microbial growth in building materials, especially in dry film coatings, by incorporating any of the claimed antimicrobial compound combinations into the materials. Typically, the antimicrobial compositions are used to inhibit growth of bacteria and/or fungi. It is contemplated that some embodiments may contain one or more additional antimicrobial compound.

EXAMPLES

Materials and Methods

The synergism of the combination of the present invention was demonstrated by testing a wide range of concentrations and ratios of the compounds.

One measure of synergism is the industrially accepted method described by Kull, F. C.; Eisman, P. C.; Sylwestrowicz, H. D. and Mayer, R. L., in *Applied Microbiology* 9:538-541 (1961), using the ratio determined by the formula:

$$Q_a/Q_A + Q_b/Q_B = \text{Synergy Index("SI")}$$

wherein:
- $Q_A$=concentration of compound A (first component) in ppm, acting alone, which produced an end point (MIC of Compound A).
- $Q_a$=concentration of compound A in ppm, in the mixture, which produced an end point.
- $Q_B$=concentration of compound B (second component) in ppm, acting alone, which produced an end point (MIC of Compound B).
- $Q_b$=concentration of compound B in ppm, in the mixture, which produced an end point.

When the sum of $Q_a/Q_A$ and $Q_b/Q_B$ is greater than one, antagonism is indicated. When the sum is equal to one, additivity is indicated, and when less than one, synergism is demonstrated. The lower the SI, the greater the synergy shown by that particular mixture. The minimum inhibitory concentration (MIC) of a microbicide is the lowest concentration tested under a specific set of conditions that prevents the growth of added microorganisms. The microorganisms tested were *Escherichia coli* (*E. coli*, ATCC #8739), a yeast, *Candida albicans* (*C. albicans*, ATCC #10231) and mold, *Aspergillus niger* (*A. niger*, ATCC #16404).

MBIT synergy with a secondary biocide was determined by evaluating the minimum biocide or biocide blend concentration required to inhibit microbial growth. All studies were conducted using a 96 well microtiter plate format. For all studies, 200 µl of microbial growth media, containing various concentrations of MBIT alone, the secondary biocide alone, or combinations of both biocide chemistries, was added to individual wells of a microtiter plate. Specifically, Tryptic Soy Broth (TSB) was utilized for bacteria (*E. coli*, ATCC #8739), Yeast Malt Extract Broth (YMB) for yeast (*Candida albicans*, ATCC #10231) and Potato Dextrose Broth (PDB) for mold (*Aspergillus niger*, ATCC #16404). Test organisms, at a final concentration of $10^4$ CFU/mL or $10^4$ spores/mL, were applied to each well in parallel experiments to initiate the MIC evaluations. Growth medium containing no biocide was utilized as a control in each experimental setup to confirm the growth viability of each organism.

Eight concentrations (2-fold dilutions) of each individual biocide were evaluated in the microbial growth inhibition studies in addition to the 64 possible combinations of these biocide concentrations. Evaluation of the individual biocide concentrations is required to achieve an inhibitory concentration end point for synergy index calculation. Following organism addition the 96-well microtiter plates were incubated at 25° C. for 48 hours or until growth was observed in the control wells containing no biocide. Individual wells were scored as growth or no growth based on visual organism growth turbidity. The lowest single active biocide concentrations resulting in no organism growth, for both MBIT and the secondary biocide, were recorded for synergy index calculations in addition to the combined biocide concentrations which resulted in an inhibition of microbial growth.

These microorganisms are representative of natural contaminants in many consumer and industrial applications. The plates were visually evaluated for microbial growth (turbidity) to determine the MIC after various incubation times at 25° C. (yeast and mold) or 30° C. (bacteria).

The test results for demonstration of synergy of the MBIT combinations of the present invention are shown below in Tables 1 and 2.

Ratios of the two biocides exhibiting synergy are presented in Tables 1 and 2.

TABLE 1

| Active Weight ratio of MBIT and Thyme | Minimum Inhibitory Concentration (ppm) | | Synergy Index |
|---|---|---|---|
| | MBIT | Thyme | |
| *E. coli* | | | |
| MBIT alone | 12.50 | 0 | QA = 12.5 |
| Thyme extract alone | 0.00 | 100,000 | QB = 100,000 |
| 1:3,968 | 6.30 | 25000 | 0.75 |
| 1:1984 | 6.30 | 12500 | 0.63 |
| 1:992 | 6.30 | 6250 | 0.57 |
| 1:496 | 6.30 | 3125 | 0.54 |
| 1:248 | 6.30 | 1562.5 | 0.52 |
| 1:124 | 6.30 | 781.25 | 0.51 |
| 1:16,129 | 3.10 | 50000 | 0.75 |
| 1:8,065 | 3.10 | 25000 | 0.50 |
| 1:4032 | 3.10 | 12500 | 0.37 |
| 1:2016 | 3.10 | 6250 | 0.31 |
| 1:504 | 3.10 | 1562.5 | 0.26 |
| 1:31,250 | 1.60 | 50000 | 0.63 |
| 1:125,000 | 0.40 | 50000 | 0.53 |
| *C. albicans* | | | |
| MBIT alone | 6.00 | 0 | QA = 6 |
| Thyme extract alone | 0.00 | 156.25 | QB = 156.25 |
| 1:52 | 1.50 | 78.125 | 0.75 |
| 1:104 | 0.75 | 78.125 | 0.63 |
| 1:208 | 0.38 | 78.125 | 0.56 |
| 1:417 | 0.19 | 78.125 | 0.53 |
| 1:833 | 0.09 | 78.125 | 0.52 |
| 1:1,667 | 0.05 | 78.125 | 0.51 |
| *A. niger* | | | |
| MBIT alone | 10.00 | 0 | QA = 10 |
| Thyme extract alone | 0.00 | 100,000 | QB = 100,000 |
| 1:40,000 | 1.25 | 50000 | 0.63 |
| 1:8,0000 | 0.63 | 50000 | 0.56 |
| 1:160,000 | 0.31 | 50000 | 0.53 |

TABLE 1-continued

| Active Weight ratio of MBIT and Thyme | Minimum Inhibitory Concentration (ppm) | | Synergy Index |
|---|---|---|---|
| | MBIT | Thyme | |
| 1:10,000 | 2.50 | 25000 | 0.50 |
| 1:20,000 | 1.25 | 25000 | 0.38 |
| 1:40,000 | 0.63 | 25000 | 0.31 |
| 1:80,000 | 0.31 | 25000 | 0.28 |

The synergistic effect of MBIT to Thyme was demonstrated at the ratio 1:52 to 1:160,000

TABLE 2

| Active Weight ratio of MBIT and Rosemary | Minimum Inhibitory Concentration (ppm) | | Synergy Index |
|---|---|---|---|
| | MBIT | Rosemary | |
| *E. coli* | | | |
| MBIT alone | 6 | 0 | QA = 6 |
| Rosemary extract alone | 0 | 25000 | QB = 25000 |
| 1:2,000 | 3 | 6250 | 0.75 |
| 1:1,000 | 3 | 3125 | 0.62 |
| 1:500 | 3 | 1562.5 | 0.56 |
| 1:250 | 3 | 781.25 | 0.53 |
| 1:8,000 | 2 | 12500 | 0.75 |

TABLE 2-continued

| Active Weight ratio of MBIT and Rosemary | Minimum Inhibitory Concentration (ppm) | | Synergy Index |
|---|---|---|---|
| | MBIT | Rosemary | |
| 1:4,000 | 2 | 6250 | 0.50 |
| 1:16,000 | 1 | 12500 | 0.62 |
| *C. albicans*: No synergy observed | | | |
| *A. niger*: No Synergy observed | | | |

Synergistic effect of MBIT to Rosemary was demonstrated at the ratio 1:250 to 1:16,000

The invention claimed is:
1. A microbiocidal composition comprising:
 (a) N-methyl-1,2-benzisothiazolin-3-one; and
 (b) at least one essential oil selected from the group consisting of thyme oil and rosemary oil;
wherein when the essential oil is thyme oil, the weight ratio of N-methyl-1,2-benzisothiazolin-3-one to thyme oil is from 1:52 to 1:160,000; and
further wherein when the essential oil is rosemary oil the weight ratio of N N-methyl-1,2-benzisothiazolin-3-one to rosemary oil is from 1:250 to 1:16,000.
2. A product comprising the microbicidal composition of claim 1.

* * * * *